United States Patent [19]

Morgan

[11] Patent Number: 5,502,067
[45] Date of Patent: *Mar. 26, 1996

[54] TREATING APNEAHYPOPNEA/SNORING IN HUMANS

[76] Inventor: Julia A. Morgan, 8398 Harvest St., Richland, Mich. 49083

[ * ] Notice: The term of this patent shall not extend beyond the expiratin date of Pat. No. 5,407,953.

[21] Appl. No.: 370,202

[22] Filed: Jan. 9, 1995

Related U.S. Application Data

[63] Continuation-in-part of Ser. No. 191,786, Feb. 4, 1994, Pat. No. 5,407,953.

[51] Int. Cl.$^6$ .................................................. A61K 31/415
[52] U.S. Cl. .................................................. 514/397
[58] Field of Search .............................................. 514/397

[56] References Cited

U.S. PATENT DOCUMENTS

| | | | |
|---|---|---|---|
| 3,826,258 | 7/1974 | Abraham | 128/268 |
| 4,248,855 | 2/1981 | Blank et al. | 424/19 |
| 4,579,960 | 4/1986 | Yuen et al. | 556/2 |
| 4,838,882 | 6/1989 | Molinoff | 604/286 |
| 4,917,674 | 4/1990 | Molinoff | 604/286 |
| 5,010,056 | 4/1991 | Boghen et al. | 514/12 |
| 5,407,953 | 4/1995 | Morgan | 514/397 |

OTHER PUBLICATIONS

Modern Medicine, Oct. 30. –Nov. 15, 1978, pp. 26–33. (re sleep disorders) Weinstein.
Lange's BASIC . . . Pharmacology, 3rd Edit., 1987, pp. 64–68. (re cholinoceptor stimulants).
PDR, 17th Edit., 1989, for Opthalmology, p. 105. (re ALZA's Ocusert$^{198}$ pilocarpine).
Korolkovas, A., Essentials of Med. Chem., 2nd Edit., 1988, pp. 114–117. (re pilocarpine esters).
The New England J. of Medicine, Apr. 29, 1993, pp. 1230–1235, (re sleep disorders) Young et al.
PDR for Opthalmology), 1993, p. 3, (re Miotics including pilocarpine Salts).
Medline Express$^{TM}$ computer search report, 6 pp., re terms "Apnea", 'Sleep Apnea syndromes' done in 1993–94.
Ehmbace abstract of Chessen et al. Diseases of the Nervous System. 35(4): 152–153 (1974) "ECT, Glaucoma, and Prolonged Apnea". (Apnea after pilocarpine eyedrops discontinued).
Goldstein, A., et al, Prin. of Drug Action, 2nd Ed., 1968 pp. 140–141. (re fatal apnea).
C&E News, Sep. 6, 1971, pp. 20, 22; (re ALZA, Ocusert$^{TM}$).

*Primary Examiner*—Shep K. Rose
*Attorney, Agent, or Firm*—John T. Reynolds

[57] ABSTRACT

This invention provides a method for treating sleep apnea, hyponea and snoring in a human patient by administering to said patient a pilocarpine compound that results in an exposure of the tissues of the naso-pharyngeal and oropharyngeal region to pilocarpine levels in an amount effective to reduce or eliminate such sleep apnea, hyponea and snoring condition in such patient during the treatment interval.

Pilocarpine hydrochloride or nitrate solutions may be applied nasally in drop form for convenience.

7 Claims, No Drawings

TREATING APNEA HYPOPNEA/SNORING IN HUMANS

REFERENCE TO PRIOR APPLICATION

This is a continuation-in part of patent application Ser. No. 08/191,786, filed Feb. 4, 1994, now U.S. Pat. No. 5,407,953, issued Apr. 18, 1995.

FIELD OF INVENTION

This invention relates to a method for treating apnea, hypopnea and snoring in human patients suffering from such conditions. More particularly, this invention provides a new medical use of known pilocarpine compounds for treating apnea, hypopnea and snoring in a human patient by the administration of a compound that results in a therapeutic amount of pilocarpine being released to relieve those apnea, hypopnea and snoring conditions in such patient during the treatment interval.

BACKGROUND OF THE INVENTION

Recent studies have shown that approximately two percent of women and four percent of men in the middle-class workforce have sleep apnea syndrome (T.Young, et al, *The New England Journal of Medicine*, p.1230,Apr. 29, 1993). The current treatment for this condition requires the use of an unwieldy positive air-pressure appliance for the rest of the patients life. No other effective non-surgical treatments have yet been devised that would alleviate these sleep-disorders.

Other publications report on research studying the effects of other drugs on sleep apnea. *The J. of Psychosom. Research.*, 1993, 3T Suppl. 1, pp 59–65 reports studies on the use of benzodiazepine hypnotic type compounds for patients with obstructive sleep apnea syndrome. However, benzodiazepine hypnotic drugs are quite potent and are not preferred by some doctors and patients because of some alleged side-effects.

*The Am. Rev. Respir. Dis.*, 19992, June, Vol.145 (6), pp 1378–83 reports on studies of gamma-hydroxybutyrate in patients with obstructive sleep apnea. No significant improvement over a control group was seen in this study.

*The Am. Rev. Respir. Dis*, 1990, February Vol 145 (2 PI 1 ), pp 435–9 reports on the effect of clonidine hydrochloride on obstructive sleep apnea in male patients. It was reported that clonidine had no effect on the frequency and duration of non-REM breathing abnormalities.

The journal, *Cardiology*, 1991, Vol.78 (1), pp 124–30, reported on the studies of the effects of antihypertensive drug agents on blood pressure in patients suffering from sleep apnea syndrome. The drugs used in the study were metoprolol, a beta-blocker, and alagapril. Although blood pressures were reduced with these drugs, the total sleep time was not statistically different between the two treated groups nor between the proportion of non-REM and REM sleep.

Other publications reporting on the effect of other medicinal agents on sleep-related snoring or sleep apnea disorders include:

a) *Drugs*, 1991; 41 Supp 1,pp 37–47 (cilazapril);

b) *Chest*, 191;August, Vol. 100 (2), pp 416–412 (protriptyline), which is used to treat obstructive sleep apnea, but has anticholinergic side-effects;

c) *Am. Res. Respir, Dis.*, 1991, November; Vol 144 (5), pp 112–1120, reports on studies of the basic mechanism of sleep-disordered breathing during rapid-eye-movement (REM) in the English bulldog.

d) *Lancet*, 1991, July 27;338 (8761); pp 251–252, (oestrodiol and medroxyprogesterone)

e) *J. Clin. Psychopharmacol.*, 1991, February, Vol. 11,(1); pp 71–72. (Buspirone)

f) *Lung,* 1990;Vol. 168 Supp, pp 948–954 (Calmitrine).

None of the above drug treatments are believed to be as effective in treating snoring, sleep apnea and hypopnea in humans as what has been discovered according to this invention.

It is an object of this invention to provide a treatment method for reducing and preferably eliminating the snoring, sleep apnea and/or hypopnea conditions in human patients suffering from such conditions with a class of drug compounds which are used for other ailments, which are safe and relatively easy to administer to the patient.

SUMMARY OF THE INVENTION

This invention provides a method for treating apnea, hypopnea and snoring in a human patient suffering from such conditions which comprises administering to the patient a pilocarpine compound resulting in the release of pilocarpine in an amount effective to reduce or eliminate such apnea, hypopnea and snoring conditions in such patient during the treatment interval. Pilocarpine can be administered by a variety of routes, e.g., ocularly or nasally, using eyedrops, pharmaceutical pilocarpine gel formulations, and the like. Presently the most readily available forms are as ocular inserts in the cul de sac of the eye and by eyedrops or by nasal drops. The preferred pilocarpine compounds are salts such as pilocarpine hydrochloride and pilocarpine nitrate. The selected pilocarpine compounds are administered nasally by placing the drug-containing matrix onto the anterior hare internal skin surface. Then, by normal inhalation or by a slight nasal pinching motion, the drug migrates onto the highly vascularized nasal mucosa, and in turn is effectively distributed to the nasal and oral pharyngeal tissue. Specific therapeutic amounts of pilocarpine thus administered may vary depending upon the concentration and diffusional properties of the drug in its matrix, as well as the physical size and physiological character of the individual. However, the pilocarpine is effective to treat the patient as soon as the drug penetrates into the peripheral tissue. Solutions of pilocarpine salts are commercially available for use in the manner described according to this invention.

DETAILED DESCRIPTION OF THE INVENTION

Formulations of pilocarpine are known by a variety of proprietary names including Adsorbocarpine, Akarpine, Isopto Carpine, Pilocar, Pilocel, Pilopine HS, P.V. Carpine and the like. The chemical name of pilocarpine is 3-ethyldihydro-4[(1-methyl-1H-imidazol- 5-yl)methyl]-2(3H)-furanone. Pilocarpine is extracted from the dried leaflets of *Pilocarpus jaborandi* or *P. microphyllus*, where it occurs to the extent of approximately 0.5 percent. Pilocarpine occurs as a viscous, hygroscopic, colorless,oily liquid, or crystals. It is soluble in water, alcohol and chloroform; it is sparingly soluble in ethyl ether, and practically insoluble in light pretoleum. Pilocarpine hydrochloride occurs as a colorless, odorless translucent, faintly bitter crystals. It is very soluble in water, freely soluble in alcohol, slightly soluble in chloroform and insoluble in ethyl ether. Pilocarpine nitrate (P.V. Carpine) occurs as shinning, white crystals; it is stable in air, being affected by light. It is freely soluble in water, sparingly soluble in alcohol, and insoluble in chloroform and ethyl ether. Aqueous solutions of pilocarpine salts, principally the chloride or nitrate, can be used according to this invention. Pilocarpine gel (Pilopine HS gel), containing pilocarpine in an aqueous gel is also available.

Pilocarpine is classified as a direct-acting cholinomimitic alklaloid it preferentially binds and activates the muscarinic receptors, producing a parasymathetic response in smooth muscle (*Basic and Clinical Pharmacology*, Katzung, B. G.,3rd Ed.,Appleton and Lange, Norwalk, Conn.,pp 63–74). It is known that pilocarpine can induce an asthmatic attack and even severe apnea by its stimulatory effect on the bronchiolar smooth muscle and the tracheobronchial mucosa, if an aerosol drug exposure occurs. The use of an apnea inducing alkaloid, such as pilocarpine, to specifically treat the symptoms of apnea represents a drug-use association that contradicts contemporary medical knowledge and is, in turn, unexpected.

If pilocarpine is administered by a pharmacokinetically selective route, e.g., through the nasal mucosa or through drainage of the ocular vasculature, the parasymapthetic effect will be generally localized, and subsequent systemic drug levels will be significantly lower, in comparison to, e.g. oral drug administration, and thus untoward side-effects are minimized.

The localized therapeutic response of the contraction of the smooth muscle of the iris sphincter and of the ciliary muscle results in the safe and common utility of pilocarpine for the treatment of the symptoms of glaucoma. Likewise, we believe that the same stimulatory effect of pilocarpine upon the smooth muscles of the nasopharnyx and oropharnyx results in an alleviation of the nasophyrangeal and/or oropharyngeal obstruction that is the apparent cause of obstructive sleep apnea (*Modern Medicine*, Oct.30, 1978, pp. 26–33.) and snoring. The localized administration of pilocarpine for the treatment of recurrent neonatal apnea, may also prove to be beneficial. The effect of pilocarpine on the mechanism of central apnea, where diaphragmatic motion is interrupted, is not known.

Applied topically to the ocular surface, pilocarpine is commonly used as a miotic of choice in the treatment of primary open-angle glaucoma, and in the emergency treatment of acute angle-closure glaucoma. Pilocarpine is also used to antagonize the effect of short-acting mydriatics of the eye.

Pilocarpine can be administered, as above described, in dosages of one or more drops of a commercially available solution or from an equivalent amount of an alternative drug containing matrix, such as a pilocarpine-containing gel.

EXAMPLE 1

This invention was discovered when a family member observed over time that a spouse, who was being treated for a glaucomatous condition with a topical miotic agent, experienced total cessation of chronic sleep apnea and snoring while on the pilocarpine-based medication. A disturbed sleep pattern of loud snoring, interrupted by frequent 20– 30 second intervals of apnea, was replaced by a quiet breathing mode with no detectable apnea episodes for the duration of the sleep cycle. A corollary effect of this disturbed sleep pattern, characterized by frequent daytime fatigue, and unavoidable early evening napping, was also observed to be eliminated while on the medication. This latter effect provides substantiating proof that the individual experienced a profound increase in the quality of night-time rest. The miotic agent used was the OCUSERT® Pilo-20 (Alza Corp., Palo Alto, Calif. 94304) brand of pilocarpine in a composition with alginic acid surrounded by a hydrophobic ethylene/vinyl acetate copolymer membrane patch which produces a slow diffusion of pilocarpine into the localized membranes.

A recurrence of apnea/snoring episodes was observed to occur when the ocular patch neared its rated time of dissipation, or if a patch was inadvertently expelled prior to scheduled replacement. These observations have maintained a consistent pattern over an extended time period, with no apparent return of the apnea/snoring symptoms while on the medication. Other medications and/or dietary involvements have been discounted as contributing factors by a process of elimination and observation.

EXAMPLE 2

The ocular route of administration of pilocarpine may present difficulty to individuals with readily irritable ocular membranes. Therefore the extension of dose administration to the nasal route was specifically investigated and was determined to be similarly useful according to this invention.

An individual human adult male suffering from the readily observable symptoms of snoring and sleep apnea, administered under the care of his physician, by the nasal route, 2–3 drops of a 4% solution of pilocarpine (Pilocar®) into each nostril several hours before sleep. Tape-recordings of the following sleep interval confirmed a significant reduction in audible snoring and an apparent cessation of apnea episodes compared to those detected on previously recorded (control) sleep intervals. This trial administration and observation was repeated over a three-night time span, with equivalent positive results. A return to snoring, irregular breathing and apnea episodes was observed to occur following cessation of the pilocarpine administration trials.

These trials did not address the multitude of specific pharmacological issues, such as bioavailablity, dose-proportionality, etc., nor the equally important drug-use safety issues such as side-effects or other drug interactions. However, the utility and similarity of targeted response using the nasal route of administration of pilocarpine to the ocular route for the treatment of the symptoms of apnea and snoring was demonstrated.

The occurance of similarity of effect by these two dissimilar routes of administration, i.e., ocular and nasal, indicates that pilocarpine availability to the vasculature and tissues of the naso- and oro-pharyngeal region, is the probable governing proccess which elicits the effective response. Thus it is conceived, by this invention, that any other route of drug administration which results in an effective amount of pilocarpine exposure (either through local or systemic influx) to this vasculature will exert a similarly effective response. The common safety and ADME (absorption, distribution, metabolism and excretion) issues that govern all routes of drug administration are addressed by well established methods which are typically performed under mandate of the drug regulatory agencies and thus are not material to this invention. Similarly, time-course profiles of the pharmacological effect will vary, depending upon the route and form of drug administration as well as the size and physiological character of the patient. These variables are also addressed by well established developmental processes and are not material to this invention.

I claim:

1. A method for treating sleep apnea and hypopnea and snoring in a human patient suffering from such conditions which comprises administering to said patient a compound resulting in the release of pilocarpine in an amount effective to reduce or eliminate such apnea and hypopnea and/or snoring conditions in such patient during the treatment interval.

2. A method according to claim 1 wherein the pilocarpine compound used to treat such patient is a pilocarpine salt.

3. A method according to claim 2 wherein the pilocarpine compound is pilocarpine hydrochloride.

4. A method according the claim 2 wherein the pilocarpine compound is pilocarpine nitrate.

5. A method according to claim 1 wherein the pilocarpine compound is administered to the patient by the nasal route.

6. A method according to claim 3 wherein the pilocarpine hydrochloride is administered by the nasal route.

7. A method according to claim 4 wherein the pilocarpine nitrate is administered by the nasal route.

* * * * *